US00PP12018P2

(12) United States Plant Patent
Rother

(10) Patent No.: US PP12,018 P2
(45) Date of Patent: Jul. 31, 2001

(54) SCAEVOLA PLANT NAMED 'BLUE SHAMROCK'

(76) Inventor: Reinhard W. Rother, 56 Emerald Monbulk Road, Emerald, Victoria, 3782 (AU)

( * ) Notice: Subject to any disclaimer, the term of this patent is extended or adjusted under 35 U.S.C. 154(b) by 0 days.

(21) Appl. No.: 09/257,097

(22) Filed: Feb. 22, 1999

(51) Int. Cl.[7] ..... A01H 5/00

(52) U.S. Cl. ..... Plt./363

(58) Field of Search ..... Plt./363

(56) References Cited

PUBLICATIONS

Huxley, A., Griffiths, M., and Levy, M., The New Royal Horticultural Society Dictionary of Gardening. vol. 4. p. 222, Jul. 10, 1992.*

* cited by examiner

*Primary Examiner*—Bruce R. Campell
*Assistant Examiner*—Michelle Kizilkaya
(74) *Attorney, Agent, or Firm*—C. A. Whealy

(57) ABSTRACT

A distinctive cultivar of Scaevola plant named Blue Shamrock, characterized by its low-growing, compact and outwardly spreading growth habit; short internodes, dense and bushy plant form and freely branching plant habit; fluoriferousness with about 150 flowers and flower buds per plant; and large blue-purple fan-shaped flowers.

1 Drawing Sheet

BACKGROUND OF THE INVENTION

The present invention relates to a new and distinct cultivar of Scaevola plant, botanically known as *Scaevola aemula* and referred to by the cultivar name Blue Shamrock.

The new cultivar is a product of a planned breeding program conducted by the Inventor in Emerald, Victoria, Australia, The objective of the breeding program was to create new compact Scaevola cultivars.

The new cultivar originated from a cross made by the Inventor in 1993 of a proprietary selection of *Scaevola aemula* identified as 93/203 as the female, or seed, parent and an unidentified selection of *Scaevola aemula* as the male, or pollen, parent. The new Scaevola was selected by the Inventor as a flowering plant within the progeny of this cross in a controlled environment in Emerald, Victoria, Australia in 1993.

Compared to plants of the female parent, the selection 93/203, plants of the new Scaevola have darker green leaves that are less serrated and have shorter internodes.

Compared to plants of the male parent, the unidentified selection of *Scaevola aemula*, plants of the new Scaevola have larger darker green leaves and longer stems.

Asexual propagation of the new cultivar by terminal cuttings taken in Emerald, Victoria, Australia, has shown that the unique features of this new Scaevola are stable and are reproduced true to type in successive propagations.

SUMMARY OF THE INVENTION

The new cultivar has not been observed under all possible environmental conditions. The phenotype may vary somewhat with variations in environment such as temperaure, daylength and light intensity, without, however, any variance in genotype.

The following characteristics have been repeatedly observed and are determined to be basic characteristics of 'Blue Shamrock' which distinguish 'Blue Shamrock' as a new and distinct cultivar:

1. Low-growing, compact and outwardly spreading growth habit.
2. Short internodes, dense and bushy plant form and freely branching plant habit.
3. Freely flowering, about 150 flowers and flower buds per plant.
4. Large blue-purple fan-shaped flowers.

Compared to plants of the *Scaevola aemula* cultivar Blue Wonder, disclosed in U.S. Plant Pat. No. 7,929, plants of the new Scaevola are more compact, fuller, denser, and have shorter internodes when grown side-by-side.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical hanging basket plant of 'Blue Shamrock'.

The photograph at the bottom of the sheet comprises a close-up view of a typical flowering stem, flower bud and open flower of plants of 'Blue Shamrock' (top) and upper surfaces of leaves showing various stages of development and leaf shapes. Flower and foliage colors in the photographs may appear different from the actual colors due to light reflectance.

DETAILED BOTANICAL DESCRIPTION

The following observations, measurements and values describe 25-cm hanging basket containers with three plants each of the new cultivar grown in Bonsall, Calif. under outdoor, full-sun conditions with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Scaevola aemula* cultivar Blue Shamrock.

Parentage:

*Female, or seed, parent.*—Proprietary selection of *Scaevola aemula* identified as 93/203.

*Male, or pollen, parent.*—Unidentified selection of *Scaevola aemula.*

Propagation:

*Type cuttings.*—Stem and terminal cuttings.

*Time to initiate roots.*—Summer: About 18 to 21 days at temperatures of 25° C. Winter: About 21 to 28 days at temperatures of 20 to 25° C.

*Rooting habit.*—Numerous and fine.

Plant description:

*Plant form and growth habit.*—Perennial container and garden plant. Low-growing, compact and outwardly spreading. Suitable for hanging basket containers. Numerous leaves and short internodes, full, dense and bushy. Freely branching with about six lateral branches; removal of terminal apices (pinching) is usually not required.

*Crop time.*—About 8 to 12 weeks are required to produce a finished, flowering plant in a 10-cm container.

*Vigor.*—Moderately vigorous.

*Plant height.*—About 16 to 25 cm.

*Plant width* (*spread*).—About 22 to 55 cm.

*Stem description.*—Length: About 54 cm. Diameter: About 4 mm. Internode length: About 1.5 to 2 cm. Color: Top, 182A; underside, 146B. Texture: Smooth, glabrous.

*Foliage description.*—Arrangement: Alternate, single. Quantity per lateral stem: About 28. Length: About 5.8 cm. Width: About 1.6 to 2 cm. Shape: Spatulate to elliptic; leaves subtending flowers are bract-like. Apex: Broadly acute. Base: Cuneate; sessile. Margin: Irregularly serrated, becoming more serrated towards leaf apex and with development. Varying and irregular serration patterns. Texture: Very sparsely pubescent; thick, somewhat succulent. Color: Young leaves, upper surface: 137A. Young leaves, lower surface: 137C. Fully expanded leaves, upper surface: 137A; base, 144B. Fully expanded leaves, lower surface: 138B. Venation, upper surface: 137A. Venation, lower surface: 138B.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers horizontal to perpendicular to stem. About 8 to 10 flowers and about 16 buds per lateral stem; freely flowering with about 150 flowers and buds per plant.

*Flowering time.*—Plants start flowering when lateral branches are about 10 cm in length; flowers open acropetally. Plants flower continuously from spring until fall.

*Flower buds.*—Shape: Tubular. Length: About 1.8 cm. Diameter: About 3 mm. Color: 147D.

*Perianth.*—Aspect: Fan-shaped, flat. Length: About 2 cm. Diameter: About 3 cm. Height: About 1.7 cm.

*Petals.*—Quantity: Five, fused at base. Shape: Elliptic. Apex: Broadly acute. Margin: Entire. Length, above tube: About 1.5 cm. Width, above tube: About 7 mm. Texture: Smooth. Color: When opening, upper surface: 86A. When opening, lower surface: 86C. Fully opened, upper surface: 86B; 8C at base with stripes of 3A (nectar guides). Fully opened, lower surface: 86C.

*Flower throat.*—Appearance: Whiskered. Length: About 1.2 cm. Diameter: About 4 mm. Color: Green-yellow, 154A, with purple, 86A to 86B, venation.

*Sepals.*—Quantity and arrangement: Two; opposite. Shape: Oblong. Length: About 1 cm. Width: About 2.5 mm. Color: Upper surface: 137A. Lower surface: 138B.

*Reproductive organs.*—Androecium: Five stamens. Anthers: Shape: Oblong. Length: About 1.5 mm. Diameter: About 0.5 mm. Color: 152C. Pollen: Scarce. Pollen color: 152C. Gynoecium: Pistil length: About 1.2 cm. Style length: About 1.1 cm. Style color: 59A to 59B. Stigma shape: Oblong with fine white hairs. Stigma color: 155C to 155D. Ovary color: 144A.

Disease resistance: Resistance to pathogens common to Scaevola has not been observed.

Seed production: Seed production has not been observed.

It is claimed:

1. A new and distinct Scaevola plant named Blue Shamrock, as illustrated and described.

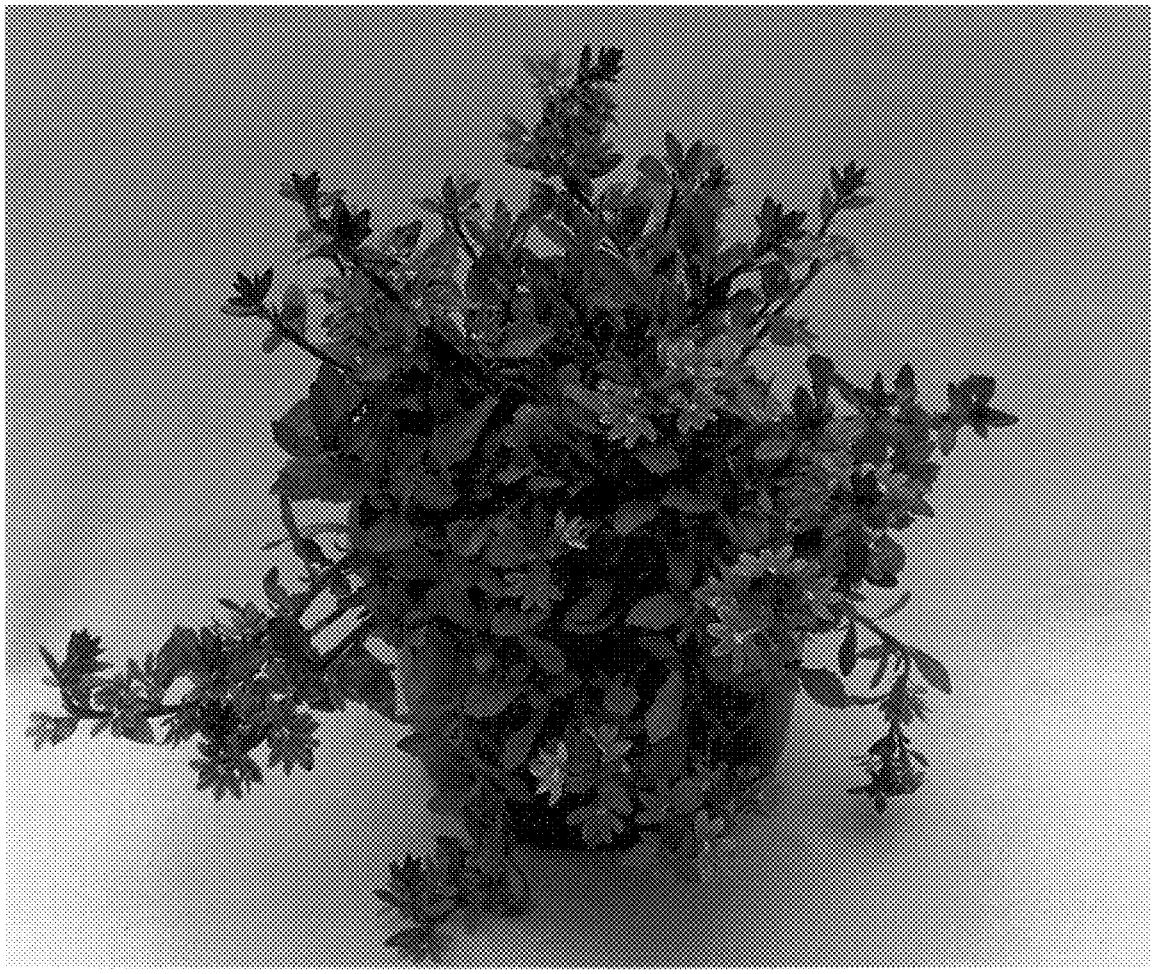
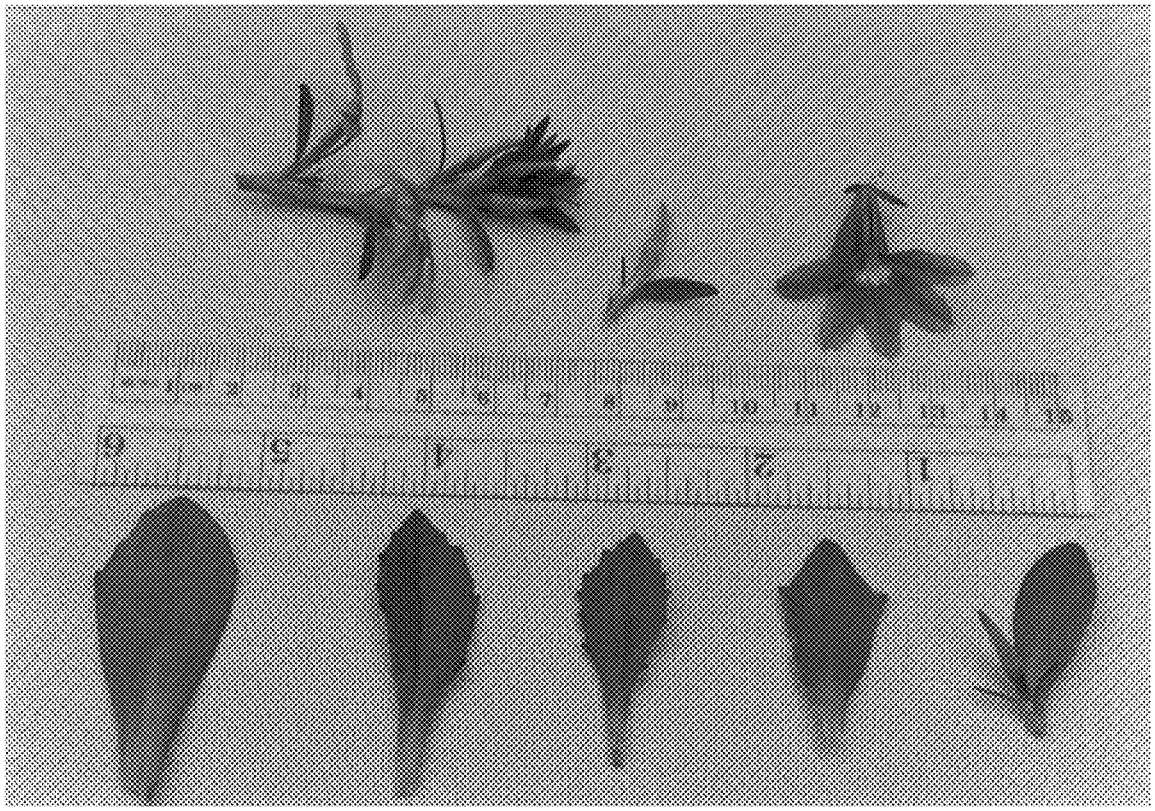

* * * * *